US008663686B2

(12) United States Patent
Zhang et al.

(10) Patent No.: US 8,663,686 B2
(45) Date of Patent: Mar. 4, 2014

(54) BIODEGRADABLE CHITOSAN-PEG COMPOSITIONS AND METHODS OF USE

(75) Inventors: Miqin Zhang, Bothell, WA (US); Narayan Bhattarai, Seattle, WA (US); Frederick A. Matsen, Seattle, WA (US)

(73) Assignee: University of Washington, Seattle, WA (US)

( * ) Notice: Subject to any disclaimer, the term of this patent is extended or adjusted under 35 U.S.C. 154(b) by 1322 days.

(21) Appl. No.: 11/124,916

(22) Filed: May 9, 2005

(65) Prior Publication Data

US 2006/0251613 A1 Nov. 9, 2006

(51) Int. Cl.
*A61K 9/00* (2006.01)

(52) U.S. Cl.
USPC ............................. 424/484; 424/486; 424/488

(58) Field of Classification Search
None
See application file for complete search history.

(56) References Cited

U.S. PATENT DOCUMENTS

| | | | |
|---|---|---|---|
| 6,027,744 A | 2/2000 | Vacanti et al. | |
| 6,432,449 B1 * | 8/2002 | Goldenberg et al. | 424/486 |
| 6,841,617 B2 | 1/2005 | Jeong et al. | |
| 6,858,222 B2 | 2/2005 | Nelson et al. | |

FOREIGN PATENT DOCUMENTS

| | | |
|---|---|---|
| EP | 0 797 615 B1 | 1/1999 |
| WO | WO 99/07417 A1 | 2/1999 |

OTHER PUBLICATIONS

Harris et al., 22 Journal of Polymer Science 341 (1984).*
Khalid et al. 9 STP Pharma. Sci. 359 (1999).*
Mi et al., 23 Biomaterials 181 (2002).*
Odian, Principles of Polymerization 3ed 1991.*
Product information for Aldrich 417963—Chitosan from shrimp shells, accessed Mar. 17, 2011.*
Molecular weight question and answer for Chitosan, Product 417963, last updated Mar. 14, 2011; accessed Mar. 17, 2011.*
Saito et al., Marcomol Rapid Commun, 18, p. 547-550, 1997.*
Wang et al. J Pharm Sci, 85(11), p. 1204-1210, 1996.*
Chenite, A., et al., "Novel Injectable Neutral Solutions of Chitosan Form Biodegradable Gels In Situ," *Biomaterials* 21:2155-2161, 2000.
Harris, J.M., et al., "Synthesis and Characterization of Poly(ethylene Glycol) Derivatives," *Journal of Polymer Science: Polymer Chemistry Edition* 22:341-352, 1984.
Jeong, B., and A. Gutowska, "Lessons From Nature: Stimuli-Responsive Polymers and Their Biomedical Applications," *TRENDS in Biotechnology* 20(7):305-311, Jul. 2002.
Jeong, B., et al., "Biodegradable Block Copolymers as Injectable Drug-Delivery Systems," *Nature* 388:860-862, Aug. 28, 1997.
Jeong, B., et al., "In Situ Gelation of PEG-PLGA-PEG Triblock Copolymer Aqueous Solutions and Degradation Thereof," *Journal of Biomedical Materials Research* 50:171-177, 2000.
Jeong, B., et al., "Thermoreversible Gelation of PEG-PLGA-PEG Triblock Copolymer Aqueous Solutions," *Macromolecules* 32:7064-7069, 1999.
Khalid, M.N., et al., "Water State Characterization, Swelling Behavior, Thermal and Mechanical Properties of Chitosan Based Networks," *European Journal of Pharmaceutical Science* 15:425-432, 2002.

(Continued)

*Primary Examiner* — Nissa Westerberg
(74) *Attorney, Agent, or Firm* — Christensen O'Connor Johnson Kindness PLLC

(57) ABSTRACT

The present invention provides compositions comprising an interpolymer of chitosan and polyethylene glycol, wherein the interpolymer is a liquid below 25° C. and a gel above 35° C. The present invention also provides methods for using the compositions to deliver drugs to a living body over time.

18 Claims, 7 Drawing Sheets

(56) References Cited

OTHER PUBLICATIONS

Kumar, M.N.V.R., et al., "Chitosan Chemistry and Pharmaceutical Perspectives," *Chemical Reviews* 104:6017-6084, 2004.

Mi, F.-L., et al., "Synthesis and Characterization of a Novel Chitosan-Based Network Prepared Using Naturally Occurring Crosslinker," *Journal of Polymer Science: Part A: Polymer Chemistry* 38:2804-2814, 2000.

Mwale F., et al., "Biological Evaluation of Chitosan Salts Cross-Linked to Genipin as a Cell Scaffold for Disk Tissue Engineering," *Tissue Engineering* 11(1/2):130-140, 2005.

Ruel-Gariépy, E., et al., "A Thermosensitive Chitosan-Based Hydrogel for the Local Delivery of Paclitaxel," *European Journal of Pharmaceutics and Biopharmaceutics* 57:53-63, 2004.

* cited by examiner

BIODEGRADABLE CHITOSAN-PEG COMPOSITIONS AND METHODS OF USE

STATEMENT OF GOVERNMENT LICENSE RIGHTS

This invention was made with government support under grant number EEC 9529161 awarded by the National Science Foundation. The government has certain rights in the invention.

FIELD OF THE INVENTION

The present invention relates to biodegradable gels, and their use as implantable drug delivery vehicles.

BACKGROUND OF THE INVENTION

In some clinical situations it is desirable to provide a portion of a living body, such as a human body, with a drug over an extended time period (e.g., days, weeks, or months). For example, it may be desirable to provide a broken, or diseased, portion of mammalian bone with a growth factor, that promotes new bone growth, during the process of bone healing. One way to provide the drug is to implant a drug delivery composition at the desired location in the living body. Some drug delivery compositions are biodegradable, exist as a gel at the temperature of the living body, but exist as a liquid below the temperature of the living body. Drug molecules can be incorporated into these compositions in their liquid form, and the compositions can thereafter be introduced into a living body where they form a gel that is degraded by the body over time, thereby releasing the drug molecules.

Synthetic polymers such as polyethylene glycol, poly(lactic acid) (PLA), and PEG-PLGA-PEG have been used as thermoreversible drug delivery systems (Jeong, B. et al., *Nature* 388:860 (1997); Jeong, B., et al., *Macromolecules* 32:7064 (1999); Jeong, B., et al., *J. Biomed. Mater. Res.* 50:171 (2000)). Natural polymers are typically more desirable than synthetic polymers for biomedical applications because of their biocompatibility and biodegradability. (Jeong, B., and A. Gutowska, *Trends Biotechnol.* 20:360 (2002); Chenite, A., et al., *Biomaterials* 21:2155 (2000)). For example, Chenite et al. (*Biomaterials* 21:2155 (2000)) developed a thermoreversible gel, composed of chitosan and glycerol-2-phosphate salts, that gels at a temperature of about 37° C., or above, depending on the amount of the salts present in the composition. In the practice of the Chenite et al. technology, the chitosan solution had to be prepared in dilute acid in order to dissolve the chitosan. Consequently, the chitosan solution had an acidic pH that is irritating to living tissue. Additionally, excess sodium glycerol phosphate (β-GP) salt was required to gel the chitosan solution. The excess β-GP salt may be harmful if it is absorbed by living tissue.

A need remains, therefore, for drug delivery compositions, made from biocompatible natural, or synthetic, polymers, that are biodegradable and that exist as a liquid below the temperature of a recipient living body, and as a gel at the temperature of the recipient living body. The liquid phase of the compositions can be loaded with drug molecules, and thereafter be introduced into a living body where they form a gel that is degraded and releases the drug over time.

SUMMARY OF THE INVENTION

In accordance with the foregoing, the present invention provides compositions comprising an interpolymer of chitosan and polyethylene glycol, wherein the interpolymer is a liquid below 25° C. and a gel above 35° C. The interpolymer is the most abundant component in the composition, and so when the interpolymer forms a gel, the composition also has the consistency of a gel, although non-gel components (e.g., drug molecules) may be present in the composition in addition to the gelled interpolymer. The compositions of the present invention are compatible with living tissue. Moreover, the compositions of the present invention can be degraded by living tissue (i.e., are biodegradable). Thus, the compositions of the present invention can be used, for example, to deliver drugs (e.g., growth factors, anti-inflammatory agents) to a living organism by incorporating (e.g., dissolving) the drug molecules into a liquid composition of the present invention and introducing (e.g., injecting) the liquid composition into a living animal body having a temperature that is at, or above, the temperature at which the interpolymer forms a gel. The liquid interpolymer gels in the animal body, and is thereafter gradually degraded by the surrounding tissues so that the drug molecules are released over time. Optionally, the polyethylene glycol/chitosan interpolymer molecules can be covalently cross-linked to each other to increase the lifetime of the gel in a living body (i.e., reduce the rate of degradation of the gel by the tissues of the body).

Accordingly, in one aspect the present invention provides compositions comprising an interpolymer of chitosan and polyethylene glycol, wherein the interpolymer is a liquid below 25° C. and is a gel above 35° C. The polyethylene glycol may be present in the interpolymer in an amount of from 30% by weight to 65% by weight based on the total weight of the interpolymer.

In another aspect the present invention provides methods for delivering a drug to a living body. The methods of this aspect of the invention include the step of delivering a composition comprising a drug to a portion of a living body, wherein: (a) the composition comprises an interpolymer of chitosan and polyethylene glycol, wherein the interpolymer is a liquid below 25° C. and a gel above 35° C.; (b) the interpolymer forms a gel after it is delivered to the living body; and (c) the composition comprises a drug that is released from the gel into the living body.

In a further aspect the present invention provides methods of promoting the growth of bone in a living body. The methods of this aspect of the invention include the step of introducing a composition comprising a growth factor into a bone, wherein:

(a) the composition comprises an interpolymer of chitosan and polyethylene glycol, wherein the interpolymer is a liquid below 25° C. and a gel above 35° C.; (b) the interpolymer forms a gel after it is delivered to the bone; and (c) the gel comprises a growth factor that promotes the growth of bone and that is released from the gel into the bone. The gel may optionally further comprise living osteoblasts, which are cells that make bone. The methods of this aspect of the invention are useful, for example, for treating osteoporosis.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

In one aspect, the present invention provides compositions comprising an interpolymer of chitosan and polyethylene glycol, wherein the interpolymer is a liquid below 25° C. and a gel above 35° C. The compositions of the present invention are biodegradable.

As used herein, the term "biodegradable" means that the compositions of the present invention are chemically and/or physically degraded by an animal body after being implanted into the animal body. The products produced by degradation of a composition of the present invention by an animal body are not toxic to the animal body.

Figure 1:
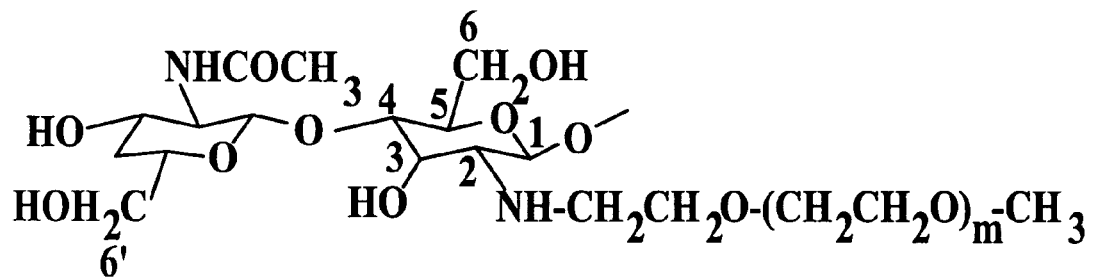
FIG. 1 shows a portion of a PEG-chitosan interpolymer molecule.

As used herein, the term "interpolymer" refers to polyethylene glycol covalently bound to chitosan, although the precise nature of the interrelationship of the polyethylene glycol and chitosan is not clearly established at this time. The term "interpolymer" excludes mere mechanical mixtures, blends, or other non-chemically bonded combinations of polyethylene glycol and chitosan. A drawing of what is believed to be the most common chemical linkage between chitosan and polyethylene glycol in the interpolymer molecules is shown in FIG. 1.

As used herein, the term "chitosan" refers to chitosan and chitosan salts. Chitosan is a deacetylated chitin having the general formula $(C_8H_{13}NO_5)_n$ and is a glucosamine polysaccharide. The degree of chitosan deacetylation typically ranges from about 55% to about 99%. The chitosan molecular weight typically ranges from about 10,000 Daltons to about 2,000,000 Daltons.

Polyethylene glycol that is useful for making the compositions of the present invention has a molecular weight in the range of from 700 Daltons to 5000 Daltons.

The compositions of the present invention are liquid below 25° C., but are gels above 35° C. The test-tube inverting method described by B. Jeong et al. (*Macromolecules* 32:7064-69 (1999), which publication is incorporated herein by reference) can be employed to determine the occurrence of the transition from liquid to gel. In the practice of the Jeong et al. method, a liquid flows within a test tube when the test tube is inverted, whereas a gel does not flow within the test tube when the test tube is inverted.

Some interpolymers used in the present invention are gels at a temperature that is below 35° C. but which is above 25° C. Thus, for example, some interpolymers used in the present invention are liquid below 25° C., but are gels above 32° C. Again by way of example, some interpolymers used in the present invention are liquid below 25° C., but are gels above 30° C. Consequently, the compositions may be injected, in liquid form, into a portion of a living body where the interpolymer forms a gel, provided that the temperature of the living body at the site of injection is equal to or greater than the temperature at which the interpolymer forms a gel. For example, the temperature of the human body is typically about 37° C.

Typically, the polyethylene glycol portion of the interpolymer is present in the interpolymer in an amount of from 30% by weight to 65% by weight (more typically from 40% by weight to 65% by weight) based on the total weight of the interpolymer. In general, larger amounts of lower molecular weight polyethylene glycol are required to effect gelation of the interpolymer, whereas smaller amounts of higher molecular weight polyethylene glycol are required to effect gelation of the interpolymer. Thus, for example, a useful amount of polyethylene glycol in the molecular weight range of 2000 to 5000 is 40% by weight to 50% by weight based on the total weight of the interpolymer. Again by way of example, a useful amount of polyethylene glycol in the molecular weight range of 700 to 1500 is 50% by weight to 65% by weight based on the total weight of the interpolymer. By way of specific example, a useful amount of polyethylene glycol having a molecular weight of 2000, or thereabout, is 45% by weight to 55% by weight based on the total weight of the interpolymer. In general, lower molecular weight chitosan requires a lower percentage of polyethylene glycol (compared to higher molecular weight chitosan) for gelation of the interpolymer to occur.

The concentration of the PEG-chitosan interpolymer in the compositions of the invention is greater than zero, and is typically up to 3 percent (by weight of the composition).

The present inventors have found that when the interpolymer molecules are covalently cross-linked to each other, then the composition including the cross-linked interpolymer molecules degrades more slowly in an aqueous environment (e.g., when implanted in a living body) than otherwise identical compositions that are not covalently cross-linked. Thus, for example, cross-linked embodiments of the gels of the present invention are particularly useful as drug delivery compositions wherein the gel, that includes drug molecules disposed within the gel, is introduced into a living body and is degraded by the living body over time (e.g., over a period of several hours, or several days, or several weeks), so that the gel thereby releases the drug molecules into the living body. Any cross-linking agent can be used that does not cause an adverse reaction (e.g., inflammation or cell death) in the living body. Representative examples of useful cross-linking agents include genipin and glutaraldehyde. Genipin is described, for example, in Mwale, F. et al., Biological Evaluation of Chitosan Salts Cross-Linked to Genipin as a Cell Scaffold for Disk Tissue Engineering, *Tissue Engineering,* 11:131-140 (2005), and Sung, H. W., et al., Cross-linking of Biological Tissues Using Genipin and/or Carbodiimide, *Journal of Biomedical Material Research A.* 65:271-82 (2003), both of which publications are incorporated herein by reference.

The amount of cross-linking agent present in the gels of the present invention is typically in the range of from about 0.5% (by weight) to about 1.5% (by weight). Typically, gels that have more crosslinkages degrade more slowly in a living body than gels that have fewer crosslinkages. Consequently, the extent of crosslinking during synthesis of the gels may be selected to achieve a desired degradation rate.

The compositions of the present inventions may be used, for example, as drug delivery compositions. Drug molecules can be introduced (e.g., by mixing) into a liquid composition of the invention, and the liquid composition containing the drug is introduced (e.g., by injection) into a portion of a living body having a temperature that causes the liquid interpolymer to form a gel. The portion of the living body surrounding the gel degrades the gel over time, so that the drug molecules are released, over time, into the living body.

In this regard, an advantage of the compositions of the present invention is that they can be prepared and used at a physiological pH that is within the range of pHs that normally occur in a living body, such as a mammalian (e.g., human) body (e.g., in the range of from pH 7.35 to pH 7.45). Physiological pH promotes the stability of many biologically active molecules that can be included in the compositions of the present invention, such as proteins, peptides, lipids, antibodies, nucleic acid molecules (e.g., oligonucleotides or other DNA molecules), carbohydrates, imaging agents, or small drug molecules. The small drug molecules can be, for example, antibacterial agents, antifungal agents, anti-inflammatory agents, anticancer agents, antiviral agents, antiprotozoan agents, analgesics, antiarrhythmics, antiandrogenics, antihelminthics, antidepressants, or antihypertensive agents.

Other examples of drugs that can be included in the compositions include cytokines such as a vascular endothelial growth factor (VEGF), endothelial cell growth factor (ECGF), fibroblast growth factor (FGF), insulin-like growth factor (IGF), bone morphogenic growth factor (BMP), platelet-derived growth factor (PDGF), epidermal growth factor (EGF), thrombopoietin (TPO), interleukins (e.g., IL1-IL15), interferons (IFN), erythropoietin (EPO), ciliary neurotrophic factor (CNTF), colony stimulating factors (e.g., G-CSF, M-CSF, GM-CSF), glial cell-derived neurotrophic factor (GDNF), leukemia inhibitory factor (LIF), or a macrophage inflammatory protein (e.g., MIP-1a, MIP-1b, MIP-2). Examples of the foregoing types of proteins are described, for example, in Norton, L. W., et al., In vitro characterization of vascular endothelial growth factor and dexamethasone releasing hydrogels for implantable probe coatings, *Biomaterials* 26:3285-97 (2005); U.S. Pat. No. 6,858,222 and U.S. Pat. No. 6,841,617, each of which publications are incorporated herein by reference.

Drugs are included in the compositions of the present invention in amounts that provide a pharmaceutically effective dosage when the drug is released from the composition over a desired time period. Pharmaceutically effective dosages of many pharmaceutical compositions are set forth, for example, in the Physicians' Desk Reference (Thomson Healthcare, 2005).

Chitosan can be covalently linked to PEG by, for example, amide linkages, imine linkages, urea linkages or carbamate linkages. Interpolymers useful in the practice of the present invention can be prepared, for example, by modifying chitosan with a polyethylene glycol-aldehyde to yield an imine (Schiff base) that is subsequently converted to a polyethylene glycol/chitosan interpolymer by reduction with sodium cyanoborohydride ($NaCNBH_3$). An exemplary procedure for chemically synthesizing compositions of the present invention is set forth in Example 2 herein. An exemplary procedure for covalently cross-linking interpolymer molecules using genipin is set forth in Example 2 herein.

In another aspect, the present invention provides methods for delivering a drug to a living body. The methods of this aspect of the invention each include the step of delivering a composition comprising a drug to a portion of a living body, wherein: (a) the composition comprises an interpolymer of chitosan and polyethylene glycol, wherein the interpolymer is a liquid below 25° C. and a gel above 35° C.; (b) the interpolymer forms a gel after it is delivered to the living body; and (c) the composition comprises a drug that is released from the gel into the living body. The methods of the present invention can be applied to any animal provided that the body temperature of the animal is sufficiently high to cause the composition to form a gel. For example, the methods of this aspect of the invention can be applied to mammals, including human beings, dogs, cats, horses, sheep, goats, and pigs.

The compositions of the present invention are useful in the practice of the methods of the present invention. The compositions can be delivered to any portion of a living body by any useful means. For example, the compositions can be injected into any soft tissue or organ of a living body. Again, by way of example, the compositions can be introduced into gaps or spaces in bone to release drugs that stimulate the growth of new bone in the gaps or spaces (e.g., the compositions can be introduced, during or after surgery, into spaces created in bone by the removal of cancerous tumors therefrom).

Thus, in a particular embodiment, the present invention provides methods for promoting the growth of bone in a living body. The methods of this aspect of the invention each include the step of introducing a composition comprising a growth factor into a bone, wherein: (a) the composition comprises an interpolymer of chitosan and polyethylene glycol, wherein the interpolymer is a liquid below 25° C. and a gel above 35° C.; (b) the interpolymer forms a gel after it is delivered to the bone; and (c) the gel comprises a growth factor that promotes the growth of bone and that is released from the gel into the bone.

Examples of growth factors that can stimulate the growth of bone include bone morphogenic growth factors (abbreviated as BMPs)(e.g., BMP 1 thru BMP 15, more specifically BMP2, BMP4, and BMP7), platelet-derived growth factor (abbreviated as PDGF), interleukins (e.g., IL1 thru IL15) and insulin like growth factor (e.g., IGF-1).

In the practice of this aspect of the invention, the composition may also include living osteoblasts, which are cells that make bone.

The methods of this aspect of the invention can be used, for example, to treat osteoporosis by promoting the growth of new bone in a bone afflicted with osteoporosis. Osteoporosis is a common bone disease in which bones become thinner and more porous. In severe cases, the bone may fracture, or cavities may appear in the bone. A composition of the present invention can be introduced (e.g., during surgery) into a broken or osteoporotic bone. The composition includes osteoblasts and at least one growth factor that stimulates the osteoblasts to make new bone, thereby strengthening the osteoporotic bone.

In a further aspect, the present invention provides a composition made by a process comprising the steps of covalently linking polyethylene glycol to chitosan to form an interpolymer of chitosan and polyethylene glycol, wherein the polyethylene glycol is present in the interpolymer in an amount of from 30% by weight to 65% by weight based on the total weight of the interpolymer, wherein the interpolymer is a liquid below 25° C. and a gel above 35° C. For example, the polyethylene glycol can be covalently linked to chitosan by modifying chitosan with a polyethylene glycol-aldehyde to yield an imine (Schiff base) that is subsequently converted to a polyethylene glycol/chitosan interpolymer by reduction with sodium cyanoborohydride ($NaCNBH_3$), as described in more detail in the Examples.

The following examples merely illustrate the best mode now contemplated for practicing the invention, but should not be construed to limit the invention.

EXAMPLE 1

This Example describes the preparation and characteristics of an interpolymer of chitosan and polyethylene glycol. In this Example, the interpolymer is referred to as PEG-grafted chitosan (abbreviated as PEG-g-chitosan).

Materials:

Chitosan and methoxy poly(ethylene glycol) (PEG) (molecular weight=2000) were obtained from Aldrich Chemical Co., and used as received. The chitosan was prepared from crab shells with 85% of deacetylation. The average molecular weight of the chitosan was 190 kDa. The Brookfield viscosity of a 1% solution of the chitosan (dissolved in 1% acetic acid) was 200-800 cps. Other reagents were all chemical grade and were used as received.

Preparation of PEG Grafted Chitosan:

PEG-grafted chitosan (abbreviated as PEG-g-chitosan) was prepared by the method of Harris et al. (*Journal of Polymer Science Part a-Polymer Chemistry*, 22:341, 1984). Chitosan was first modified with a PEG-aldehyde to yield an imine (Schiff base) that was subsequently converted to PEG-g-chitosan through reduction with sodium cyanoborohydride ($NaCNBH_3$). FIG. 1 shows a portion of a PEG-g-chitosan molecule showing what is believed to be the predominant type of covalent linkage between PEG and chitosan.

To prepare PEG-aldehyde, acetic anhydride and methoxy PEG with a molar ratio of 12/1 were added into a mixture of anhydrous DMSO and chloroform (90/10 v/v). The mixture was stirred for 12 hours at room temperature under nitrogen, and the resultant PEG-aldehyde was precipitated by addition of excess diethyl ether. The PEG-aldehyde and chitosan, having a molar ratio from 0.4 to 1, were added into a mixture of acetic acid and methanol (2/1 v/v). Aqueous cyanoborohydride ($NaCNBH_3$) solution was then added dropwise into the mixture of chitosan and PEG-aldehyde at pH 6 with a molar ratio of $NaCNBH_3$ to PEG-aldehyde ranging from 0.3 to 2. The resultant mixture was dialyzed with a dialysis membrane (MW 12000 to 14000 cut) against 0.05 M aqueous NaOH solution and freeze-dried. PEG-g-chitosan was obtained by removal of unreacted PEG from the freeze-dried samples with excess acetone. By changing the molar ratio of PEG-aldehyde to sodium cyanoborohydride, PEG-g-chitosan samples with different weight percentages of PEG were obtained, and those described in the present study are shown in Table 1.

TABLE 1

| Sample No | Molar ratio of PEG-aldehyde/ chitosan | Molar ratio of NaCNBH3/ PEG-aldehyde[a] | wt % of PEG in PEG-g-chitosan[b] |
|---|---|---|---|
| G1 | 0.4 | 0.3 | 45 |
| G2 | 0.6 | 0.3 | 55 |
| G3 | 1 | 0.3 | 64 |
| G4 | 1 | 0.1 | 68 |
| G5 | 1 | 2.0 | 36 |

[a]5M stock solution of $NaCNBH_3$ in 1M NaOH was used after being diluted with water to 3 times the original volume.
[b]The weight percentage (wt %) of PEG in PEG-g-chitosan was calculated from the relation: $(W_f - W_c)/W_f \times 100$, where $W_f$ is the weight of freeze-dried PEG-g-chitosan and $W_c$ is the weight of chitosan that was added to the reaction to synthesize PEG-g-chitosan.

The data shown in Table 1 shows that by keeping the amount of $NaCNBH_3$ roughly constant (G1 through G4), the amount of PEG incorporated into PEG-g-chitosan increased with the increase of the ratio of PEG-aldehyde to chitosan. On the other hand, excess $NaCNBH_3$ reduced the amount of PEG incorporated into PEG-g-chitosan (G5), presumably because the excess amount of $NaCNBH_3$ made the solution more basic, a pH at which chitosan is less soluble thereby hindering the chemical reaction (K. Kurita, *Prog. Polym. Sci.*, 26:1921, 2001).

Characterization of PEG-g-Chitosan:

The chemical bonding between chitosan and PEG in PEG-g-chitosan was confirmed with $^1$H-NMR. $^1$H-NMR spectra were acquired with a Bruker AV-301 spectrometer. Samples of 10-20 mg each were dissolved in 0.7 ml of $D_2O$ with addition of one drop of 0.5 M DCl in $D_2O$.

Wide angle X-ray diffraction measurements were carried out at room temperature using a diffractometer (Philips 1820 XRD, Shimdzu Co. Japan) with CuKα radiation, operated at 40 kV, 20 mA. The diffraction patterns were acquired over a diffraction angle of 2θ=5° to 45°.

For infrared spectroscopic analysis, a dried sample of 5 mg was mixed with 300 mg dry KBr and pressed into a pellet using a macro KBr die kit. The solid pellet was placed in a magnetic holder, and the system was purged with nitrogen before testing. Polarized Fourier Transformed Infrared (FTIR) spectra of 200 scans at 4 cm$^{-1}$ resolution were obtained using a Nicolet 5DX spectrometer equipped with a DTGS detector and a solid transmission sample compartment. Spectrum analyses and display were performed using standard Nicolet and Microcal Origin software.

Gel Preparation and Gelation Study:

Water soluble PEG-g-chitosan was mixed with double distilled water to make solutions of different polymer weight concentrations. The resulting solution was left overnight in a refrigerator at 4° C. The mixture was vortexed several times. The solution was centrifuged or placed under mild vacuum for one hour to remove air bubbles. 2 ml of solution were placed in a 10 ml tube with an inner diameter of 12 mm and tightly capped with a rubber septum. The solutions were maintained at a temperature between 5-10° C. prior to sol-gel transition study. A simple test-tube inverting method was employed to determine the sol-gel transition (B. Jeong et al., *J. Biomed. Mater. Res.*, 50:171, 2000).

Viscosity Measurements:

Thermoreversible gelation behavior of PEG-g-chitosan was also studied by measuring the solution viscosity of samples at neutral pH as a function of time and temperature using a Haake Viscometer (VT550) equipped with SP2P sensors. The solution was placed in the rotor of a viscometer operated at a fixed spindle speed of 30 rps and temperature was maintained using a water bath circulator. Measurements were made in the temperature range of 10 to 45° C.

Results:

The $^1$H-NMR spectra of PEG-grafted chitosan and pure chitosan were analyzed and compared. The assignments and chemical shifts of chitosan are δ 4.9-5.2 (1H br, H-1), 3.7-4.2 (br, H-3, H-4, H-5, H-6 and H-6'), 3.4 (0.85H, br s, H-2), 2.2 ppm (0.4H, br s, NHAc). The assignments and chemical shifts of PEG-grafted chitosan are: δ 5-5.3 (1H, br, H-1 of GlcN), 5.38 (br, 0.15H, H-1 of N-alkylated GlcNAc), 3.7-4.3 (m, H-3, H-4, H-5, H-6, H-6', N—CH$_{2b}$— of N-alkylated PEG and singlet of —OCH$_2$— of PEG), 3.6 (—OCH$_3$), 3.4-3.52 (0.85H, br s, H-2), 2.25 ppm (0.4H, br s, NHAc). Compared to chitosan, the peaks of PEG-grafted chitosan in the range of 3.6-4.25 ppm were not well separated due to the overlap of the more intense peak of PEG methylene groups with those of the saccharide backbone of chitosan. The methyl group of PEG in PEG-grafted chitosan was seen clearly at 3.6 ppm. Furthermore, H-1 of GlcN proton signal from chitosan shifted from δ=4.1 to 5.2 ppm after the chitosan was grafted with PEG, and the H-2 proton signal shifted from δ=3.4 to 3.5 ppm. These shifts correspond to N-alkylation of chitosan (H. Sashiwa et al., *Biomacromolecules* 4:1250, 2003).

Chitosan is a semicrystalline polymer, whereas PEG is highly crystalline with a well-defined crystal structure. The X-ray diffraction pattern of a PEG sample had strong reflection peaks at 18.74° and 22.86° and weak reflection peaks at 26.77°, 30.5°, 35.9°, and 40°, indicative of its crystalline nature (D. O. Corrigan et al., *Int. J. Pharm.* 235:193, 2002). Chitosan has a reflection at 19.7° and a relatively weak reflection at 10.2°. For PEG-g-chitosan with 45% PEG grafted (sample G1 in Table 1), the peaks associated with PEG were absent and the reflection at 19.7° for chitosan was also decreased. This observation indicates that nearly all the chitosan and PEG in sample G1 have been converted to PEG-grafted chitosan. The broad band observed at 10 to 24° with absence of intense characteristic peaks of PEG indicates that the crystalline structures of chitosan PEG were disrupted by the chemical bonding between the two polymers, thereby improving the water solubility of the material.

A comparative IR spectrum study of PEG-g-chitosan, chitosan, and PEG confirmed the success of grafting PEG to chitosan. The chitosan IR spectrum exhibited characteristic bands of 1664 cm$^{-1}$ (amide I), 1580 cm$^{-1}$ (amide II) and 1380 cm$^{-1}$ (amide III). The absorption bands at 1160 cm$^{-1}$ (asymmetric stretching of C—O—C bridge), 1075 and 1033 cm$^{-1}$ (C—O stretching) were characteristics of its saccharine structure (K. Kurita, *Prog. Polym. Sci.*, 26:1921-71, 2001; X. Qu et al., *Polymer* 41:4589-98, 2000; P. Kolhe and R. M. Kannan, *Biomacromolecules* 4:173-80, 2003). N—H and O—H stretching vibrations were characterized by the broad band in the region of 3200-3500 cm$^{-1}$. Pure PEG has characteristic peaks at 1280, 947, and 843 cm$^{-1}$ (X. Qu et al., *Polymer* 41:4589-98, 2000; P. Kolhe and R. M. Kannan, *Biomacromolecules* 4:173-80, 2003). For the PEG-g-chitosan sample, the peaks corresponding to the hydroxyl group, amino group and amide group of chitosan shifted slightly, and their intensities were significantly reduced as a result of PEG grafting. Compared to the amide I peak at 1664 cm$^{-1}$, the peak intensity of amide II significantly decreased. This resultant spectrum shows that the —NH$_2$ groups of chitosan were partially grafted with PEG. If the chitosan were fully grafted, the peaks corresponding to —NH$_2$ groups at 1580 cm$^{-1}$ would disappear and form a single peak after completion of the reaction. The characteristic peaks associated with PEG in PEG-g-chitosan at 1280, 947, and 843 cm$^{-1}$ were significantly decreased. The peaks at 1120 and 2880 cm$^{-1}$ in PEG-g-chitosan were attributable to the superposition of C—O and C—H stretching vibrations of chitosan and PEG.

To investigate the effect of the amount of PEG present in PEG-g-chitosan on the thermoreversible property of PEG-g-chitosan, the viscosity of PEG-g-chitosan solutions was measured as a function of temperature and time, respectively. The samples were dissolved in deionized water at a temperature below 10° C. to prepare aqueous solutions of different polymer concentrations. The pH of the solution can be adjusted to desired values by changing the pH of the solvent (DI water). Unlike chitosan whose solubility is highly pH-dependent, the solubility of PEG-g-chitosan was found to be less sensitive to a change in pH (tested up to pH 8.5) when sufficient PEG was present in the PEG-g-chitosan (>36%). The subsequent discussion of the results in this Example refers to PEG-g-chitosan solutions having a pH=7.4.

Figure 2:
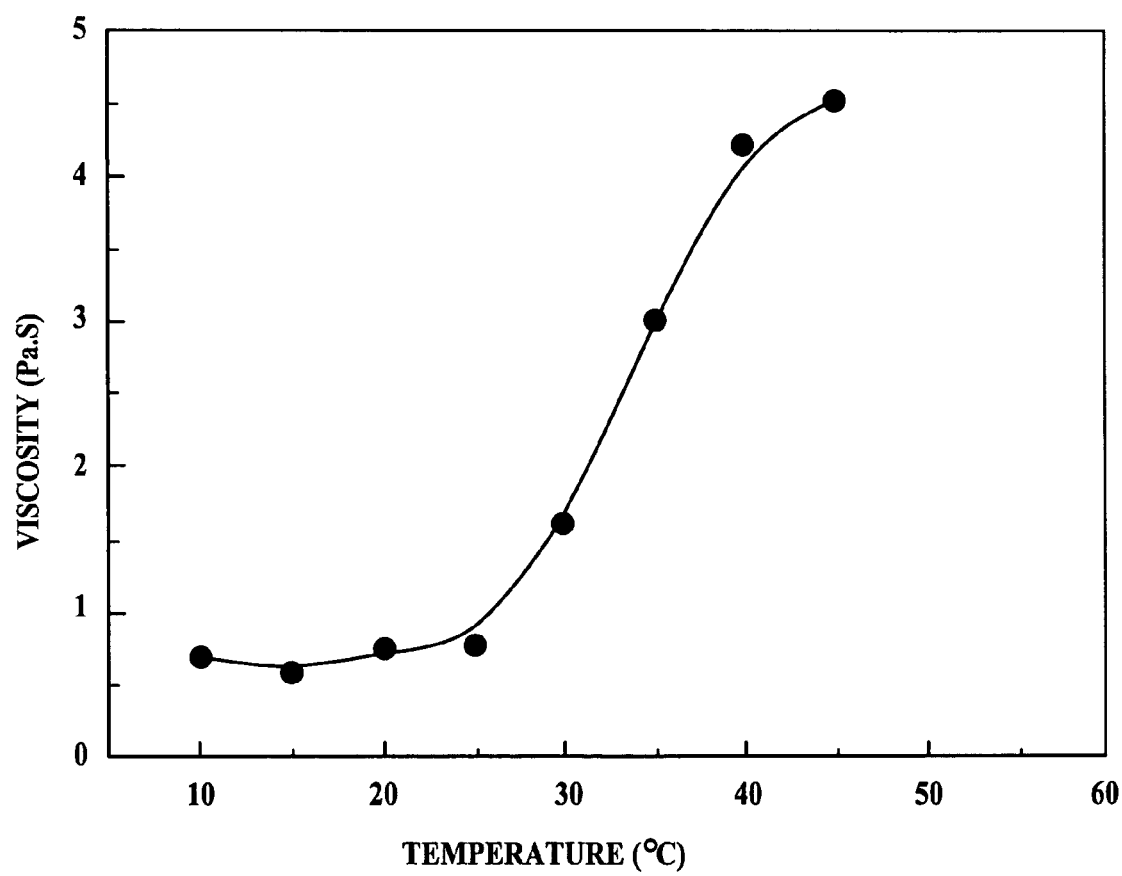
FIG. 2 shows a graph of viscosity versus temperature for PEG chitosan interpolymer sample G2 (described in Example 1) having a PEG chitosan interpolymer concentration of 3 weight percent.
Figure 3:
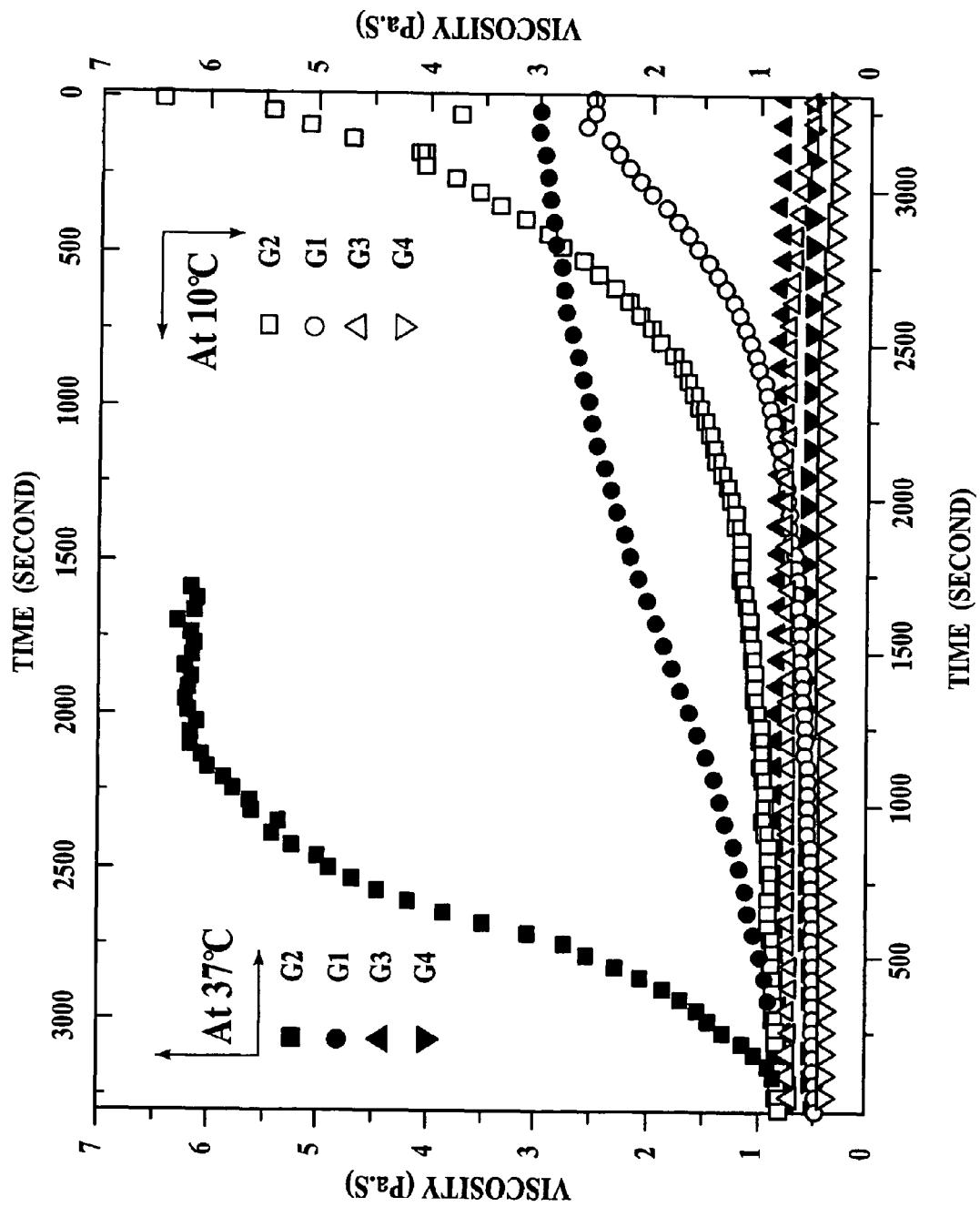
FIG. 3 shows a graph of viscosity versus time for PEG chitosan interpolymer solutions G1, G2, G3 and G4 (described in Example 1). The filled symbols correspond to the solutions maintained at 37° C., and the open symbols correspond to the solutions maintained at 10° C. The G1 solution had a polymer concentration of 1.35 wt %, and G2 through G4 solutions had a polymer concentration of 3 wt %.

Sample G5 (Table 1), with 36 wt % of PEG in the PEG-g-chitosan, was found to be barely soluble in water. Samples G1 and G2 were soluble in water when dissolved at concentrations up to 3 wt %, above which the solution was too viscous to be injectable. Aqueous solutions of samples G1 and G2, having PEG-g-chitosan concentrations of 1.3 wt % and 3 wt %, respectively, underwent an apparent sol-to-gel transition with increasing temperature. FIG. 2 shows a graph of viscosity versus temperature for sample G2, and shows the sol-to-gel transition of PEG-g-chitosan (sample G2), where an abrupt increase in viscosity at 25° C. marks the onset of the gelation process. Below the transition temperature, the sample was a solution injectable through a 22-gauge syringe needle. As the solution was heated to above the transition temperature, it transformed into a transparent gel. The gel reverted back to a solution when temperature dropped to 10° C. or below. FIG. 3 shows a graph of viscosity versus time for samples G1, G2, G3 and G4 at fixed temperatures of 37° C. (gelation) and 10° C. (liquidation). As shown in FIG. 3, the thermal responses of samples G1 and G2 were distinctly different from those of samples G3 and G4. For samples G1 and G2, the viscosity increased or decreased greatly over time, whereas there was no apparent change in viscosity for samples G3 and G4. By studying the gelation behavior of PEG-g-chitosan solutions of various polymer concentrations, we found that the gelation time varied greatly, from 10 min to 1 hour, with solutions of high polymer concentrations gelling faster than those with low polymer concentrations. Samples G1 and G2 shown in FIG. 3 are examples of those polymers whose PEG-to-chitosan ratios led to thermoreversible gelation when the solutions were prepared with appropriate polymer concentrations. Typically, solutions with a polymer concentration of 3 wt % gelled in 10 to 20 minutes.

Samples with incremental differences in the amount of PEG present in the PEG-g-chitosan were prepared and studied to determine the minimum and maximum amounts of the PEG in the PEG-g-chitosan that would result in the desired gelation characteristics. It was found that the required minimum amount of PEG to make PEG-g-chitosan soluble in water is about 36 wt %. On the other hand, an excessive amount of PEG (e.g., samples G3 and G4 with PEG wt %>55)

suppresses hydrophobic interactions between chitosan chains resulting in a solution that is not gelable at human body temperature. When the amount of PEG in PEG-g-chitosan was more than 36 wt %, but less than 45 wt %, the viscosity was so high that the solution was non-injectable at room temperature. Together, these results showed that the injectable, thermoreversible, polymers were obtained when PEG in an amount of 45 to 55 wt % was grafted to chitosan.

While not wishing to be bound by theory, the following possible gelation mechanism may account for the sol to gel transition of the PEG-g-chitosan. At low temperatures, PEG-g-chitosan chains are covered with water molecules attached by hydrogen bonds between hydrophilic groups of PEG and water molecules. Thus, the direct association between the PEG-g-chitosan chains is disrupted, rendering the PEG-g-chitosan composition soluble in water. With increasing temperature, both chitosan and PEG polymer chains gradually lose the attached water molecules, and the interactions between PEG-g-chitosan polymer chains start to prevail and a gel forms. The associative forces involved in the PEG-g-chitosan system can include hydrophobic interaction between chitosan polymer chains, hydrogen bonding between OH and $NH_2$ groups of chitosan, and intermolecular bonding between PEG chains.

Aqueous solutions of PEG-g-chitosan with pH other than 7.4 were also prepared to study sol-gel transition temperature and gelation time. Similar thermoreversible behavior was observed for the solutions with pHs ranging from 6.4 to 8.5. These pH-insensitive gelation characteristics provide great flexibility in clinical practice.

EXAMPLE 2

This Example describes the preparation and characteristics of an interpolymer of chitosan and polyethylene glycol, and the ability of the interpolymer to release protein over time. In this Example, the interpolymer is referred to as PEG-grafted chitosan (abbreviated as PEG-g-chitosan).

Materials:

Chitosan and methoxy poly(ethylene glycol) (PEG) (molecular weight=2000) were obtained from Aldrich Chemical Co., and used as received. The chitosan was prepared from crab shells with 85% of deacetylation. The average molecular weight of the chitosan was 190 kDa. The Brookfield viscosity of a 1% solution of the chitosan (dissolved in 1% acetic acid) was 200-800 cps. Bovine serum albumin (BSA) was obtained from Aldrich Chemical Co., and used as received. Genipin was obtained from Challenge Bioproducts Co., Taiwan. All other reagents were chemical grade and used as received.

Synthesis of PEG-g-chitosan:

The PEG-g-chitosan was prepared and characterized as described in Example 1.

In Vitro Protein Release Study:

Different amounts of BSA were dissolved in 1.5 ml deionized distilled water to obtain BSA solutions with final concentrations ranging from 200 to 1000 μg/ml. Solutions were prepared in 15 ml polypropylene tubes wherein 35 mg of the PEG-g-chitosan were mixed into each BSA solution and the mixtures were left overnight in a refrigerator at 4° C. After light vortexing of the polymer/protein mixtures, air bubbles were removed by centrifugation. The solutions containing PEG-g-chitosan and BSA were incubated at 37° C. for 10 minutes to form gels, and 7 ml of phosphate buffered saline (PBS, pH=7.4) was added to each tube. The gels stuck on the walls of the tubes were removed gently with a spatula and transferred into the release media. At specified sample collection times, 1 ml solution out of 7 ml total solution was removed and transferred to a siliconized 1.5 ml microcentrifuge tube, and the medium in the tube was replenished with 1 ml of fresh PBS. The protein content of each sample was analyzed using a modified Coomassie blue protein assay (Biorad®) in a 96-well plate using UV spectroscopy at 590 nm. A calibration curve was generated at each time interval using a non-loaded gel in order to correct for the intrinsic absorbance of the polymer. Samples in triplicate were analyzed for each experiment.

To achieve prolonged protein release, PEG-g-chitosan gels containing BSA were cross-linked with genipin. 1.5 ml of each PEG-g-chitosan/BSA solution were mixed with a 0.5 mM genipin solution at 4° C. and the mixture was kept at 37° C. for either 10 minutes or 24 hours, before PBS was added to the mixture. Protein release studies were carried out at 37° C. for the resulting gels.

Microscopy Analysis:

Samples for the protein release study were frozen in liquid nitrogen and freeze-dried for 24 hours. The samples were coated with gold/palladium and the morphology was examined using a scanning electron microscope (SEM) (JEOL 5200).

Analysis of Released Proteins by High Performance Liquid Chromatography (HPLC) and Gel Electrophoresis (SDS-PAGE):

To examine the stability of the protein in the gel environment, and the possible influence of the crosslinking agent on protein integrity (or aggregation), the protein released from the gels was analyzed using a high-performance liquid chromatography (HPLC) system equipped with a Rheodyne 7725i injection valve (Beckman Coulter, Rheodyne, Rohnert Park, Calif.), a System Gold Solvent Module (126), and UV Detector (168; Beckman Coulter, Fullerton, Calif.). A strong anion-exchange chromatographic column, Biosuite™ Q 10 μm AXC, 75×7.5 mm (Waters, Milford, Mass.), was used. The stationary phase had a pore size of 1000 Å and the protein capacity was specified at 331 mg/column. Detection was performed with UV absorbance at 280 nm. The mobile phases were 20 mM Tris-HCl pH 8.0 (Eluent A) and a 1 M sodium chloride solution in Eluent A (Eluent B). The flow rate was 0.8 ml/min and the gradient was 0 to 80% of Eluent B over 15 minutes. The sample volume was 20 μl. The concentration of the samples was maintained at about 2 mg/ml. Duplicate measurements were made for each sample. The experiments were performed at ambient room temperature. All calculations were performed using 32 Karat Software (Beckman Coulter, Fullerton, Calif.).

The structural integrity of BSA released from PEG-g-chitosan gels with and without genipin crosslink was also examined using a Bio-Rad Mini-Protean III electrophoresis system. All the BSA solutions prepared for the HPLC experiments were used for the 4-15% SDS-PAGE study. The BSA sample solutions were directly loaded into the wells with a micropipette, and the electrophoresis was performed at 200 V, 100 mA. The gel was stained with 0.1% Coomassie Brilliant Blue to visualize protein bands. The study was conducted according to the manufacturer's protocol. The gel pictures were taken with a scanner after wiping off all the water from the gel membrane.

Synthesis of PEG-g-Chitosan:

Chitosan was reacted with a PEG-aldehyde to yield an imine (Schiff base) and subsequently converted to PEG-grafted chitosan (PEG-g-chitosan) through reduction with sodium cyanoborohydride ($NaCNBH_3$) (K. Kurita, *Prog. Polym. Sci.*, 26:1921-71, 2001). Purified PEG-g-chitosan was analyzed by $^1HNMR$. Compared to $^1H$-NMR spectrum of chitosan, peaks in the PEG-g-chitosan spectrum in the range of 3.6-4.5 ppm were not well separated due to the overlapping of a more intense peak of PEG methylene group and peaks of saccharine backbone of chitosan. Methyl group of PEG was clearly observed at 3.6 ppm. Furthermore, the H-1 proton signal from chitosan shifted from δ=4.9 to 5.2 ppm after the chitosan was grafted with PEG, and the H-2 proton signal shifted from δ=3.4 to 3.5 ppm. These shifts correspond to N-alkylation of chitosan. (H. Sashiwa et al., *Biomacromolecules* 4:1250-54, 2003). The degree of PEG substitution (DS) was evaluated from the relative peak intensities of the methylene group of PEG and the H-1 of monosaccharide residue in $^1$H-NMR spectra. (M. Sugimoto et al., *Carbohydr. Polym.*, 36:49-59, 1998). By changing the molar ratio of PEG-aldehyde to sodium cyanoborohydride, samples with different weight percentages of grafted PEG were obtained (Table 2).

TABLE 2

| SAMPLE NO. | [PEG-ALDEHYDE]/ [CHITOSAN] | [NaCNBH3]/[PEG-ALDEHYDE][a] | DS[b] | GRAFT WT %[c] | Δη[d] (PA · S) |
|---|---|---|---|---|---|
| G36 | 1 | 2 | 0.08 | 36 | — |
| G45 | 0.4 | 0.3 | 0.16 | 45 | 2.2 |
| G55 | 0.6 | 0.3 | 0.25 | 55 | 5.2 |
| G64 | 1 | 0.3 | 0.26 | 64 | 0.02 |
| G68 | 1 | 0.1 | 0.30 | 68 | 0.03 |

[a]5M stock solution of NaCNBH$_3$ in 1 M NaOH was used after being diluted with water to 3 times the original volume.
[b]Degree of PEG substitution (DS) on chitosan backbone as determined from $^1$H-NMR spectra.
[c]Graft weight % (weight percentage of PEG in PEG-g-chitosan) was calculated from the relation: ($W_t - W_c$)/$W_t$ × 100, where $W_t$ is the weight of freeze-dried PEG-g-chitosan, and $W^c$ is the weight of chitosan that was added to the reaction to synthesize PEG-g-chitosan.
[d]Viscosity difference of the aqueous solution (pH = 7.5) of PEG-g-chitosan at two temperatures, 10° C. and 37° C. The concentration of the solution ranged from 1.35 to 3 wt %. Viscosity was measured by a Haake Viscomer at a fixed shear rate.

The data shown in Table 2 indicates that by keeping the amount of NaCNBH$_3$ roughly constant (G45 through G68), the amount of grafted PEG increased as the ratio of PEG-aldehyde to chitosan increased. On the other hand, excess NaCNBH$_3$ reduced the amount of PEG grafting (G36), perhaps because the excess amount of NaCNBH$_3$ made the solution more basic, and chitosan is less soluble at basic pH.

The results in Table 2 also show that PEG-g-chitosan that is soluble in water was obtained by grafting an appropriate amount of PEG onto a chitosan backbone. All the samples except G36, which has the lowest amount of grafted PEG, were soluble in water at physiological pH. Viscosities of all these soluble polymers were also measured at two different temperatures. Viscosity differences at the two temperatures shown in the last column of Table 2 indicate that the viscosities of samples G45 and G55 differ significantly at 37° C. and 10° C., and the viscosities increased with increasing temperature. These observations suggest an inversed thermal relation between solution viscosity and temperature, which is the basis of formation of a thermoreversible gel. Thus, only these two samples (G45 and G55) were subsequently, extensively, studied as potential candidate injectable gels.

A comparative IR spectrum study of PEG-g-chitosan, chitosan, and PEG confirmed the success of grafting PEG to chitosan. The chitosan IR spectrum exhibited characteristic bands of 1664 cm$^{-1}$ (amide I), 1580 cm$^{-1}$ (amide II) and 1380 cm$^{-1}$ (amide III). The absorption bands at 1160 cm$^{-1}$ (asymmetric stretching of C—O—C bridge), 1075 and 1033 cm$^{-1}$ (C—O stretching) were characteristics of its saccharine structure (K. Kurita, *Prog. Polym. Sci.*, 26:1921-71, 2001; X. Qu et al., *Polymer* 41:4589-98, 2000; P. Kolhe and R. M. Kannan, *Biomacromolecules* 4:173-80, 2003). N—H and O—H stretching vibrations were characterized by the broad band in the region of 3200-3500 cm$^{-1}$. Pure PEG has characteristic peaks at 1280, 947, and 843 cm$^{-1}$ (X. Qu et al., *Polymer* 41:4589-98, 2000; P. Kolhe and R. M. Kannan, *Biomacromolecules* 4:173-80, 2003). For the PEG-g-chitosan sample, the peaks corresponding to the hydroxyl group, amino group and amide group of chitosan shifted slightly, and their intensities were significantly reduced as a result of PEG grafting. Compared to the amide I peak at 1664 cm$^{-1}$, the peak intensity of amide II significantly decreased. This resultant spectrum shows that the —NH$_2$ groups of chitosan were partially grafted with PEG. If the chitosan were fully grafted, the peaks corresponding to —NH$_2$ groups at 1580 cm$^{-1}$ would disappear and form a single peak after completion of the reaction. The characteristic peaks associated with PEG in PEG-g-chitosan at 1280, 947, and 843 cm$^{-1}$ were significantly decreased. The peaks at 1120 and 2880 cm$^{-1}$ in PEG-g-chitosan were attributable to the superposition of C—O and C—H stretching vibrations of chitosan and PEG.

Thermoreversible Gelation Behavior:

Both G45 and G55 samples (Table 2) of PEG-g-chitosan, with 45 and 55 wt % of PEG grafted to chitosan, respectively, underwent an apparent sol-to-gel transition in the solutions with polymer concentrations ranging from 1.3 to 3 wt %. Below the transition temperature, the solutions were viscous liquids that flowed easily and were injectable through a 20-gauge needle. As the solutions were heated to body temperature, they transformed into gels. The gels reverted back to solutions when temperature dropped to 10° C. or below. This behavior was observed by tilting or inverting the test tube containing the gel at different temperatures. The typical sol-to-gel transition time was 10±4 minutes.

Figure 4A:
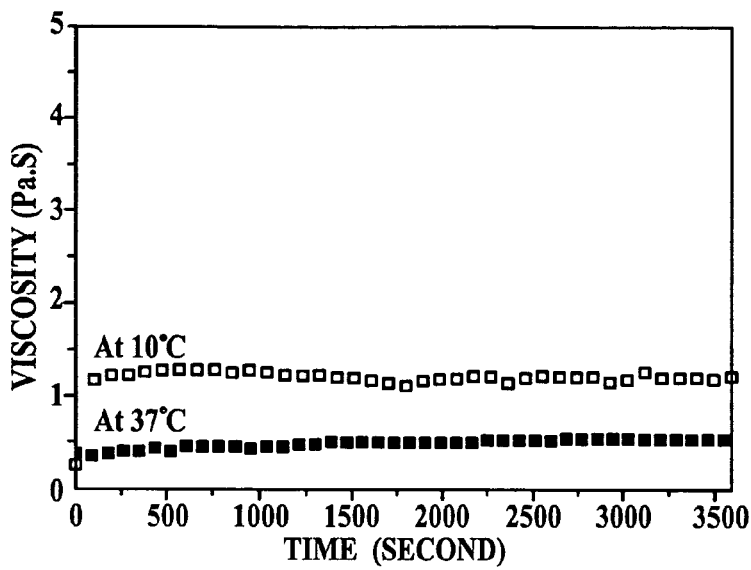
FIGS. 4A-C shows graphs of viscosity versus time, at fixed temperatures of 10° C. and 37° C., for solutions of pure chitosan (FIG. 4A) and PEG-g-chitosan samples G45 (FIG. 4B) and G55 (FIG. 4C) described in Example 2. The filled symbols refer to the solutions at 37° C., and the open symbols refer to the solutions at 10° C. Polymer concentration of pure chitosan, G45 and G55 were 3, 1.3 and 3 wt %, respectively.
Figure 4B:
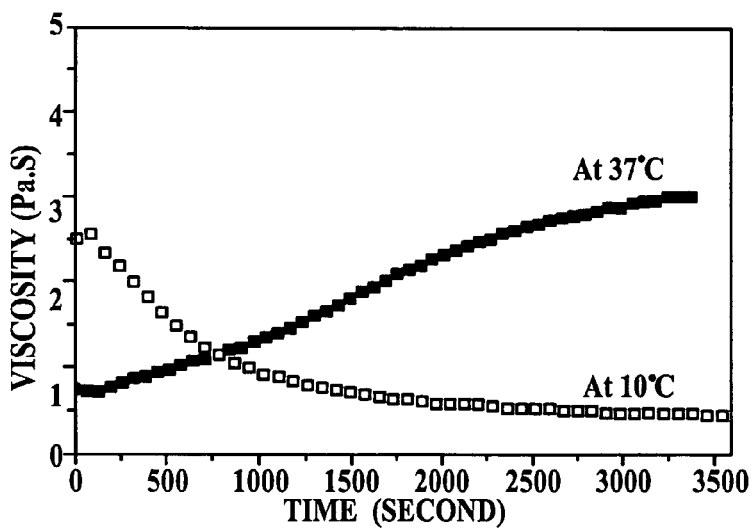
Figure 4C:
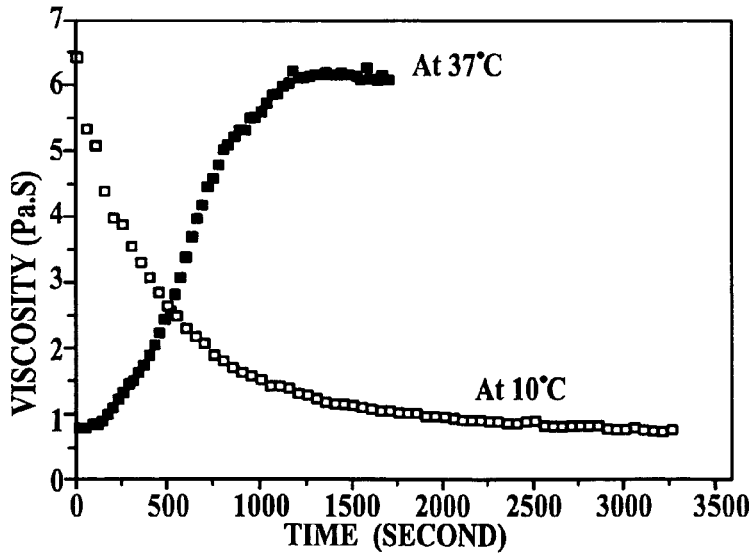

Sol-gel transition behavior of PEG-g-chitosan was further illustrated by rheological analysis. FIGS. 4A-C show graphs of viscosity versus time, at fixed temperatures of 10° C. and 37° C., for solutions of pure chitosan and PEG-g-chitosan samples G45 and G55. The chitosan solution was prepared in dilute acetic acid, and the pH was maintained at 5.7±0.2 by slowly adding a dilute solution of NaOH, whereas solutions of G45 and G55 were prepared in doubly distilled water at pH 7.4±0.5. By studying gelation behavior of PEG-g-chitosan solutions of various polymer concentrations, it was found that solutions with high polymer concentrations gelled faster than those with low polymer concentrations. Samples G45 and G55 shown in FIGS. 4B and 4C are representatives of those polymers whose PEG-to-chitosan ratios led to thermoreversible gelation when the solutions were prepared with proper polymer concentrations. Although the viscosity data for 3 wt % pure chitosan solution is shown, no apparent phase transition was observed.

Figure 5A:
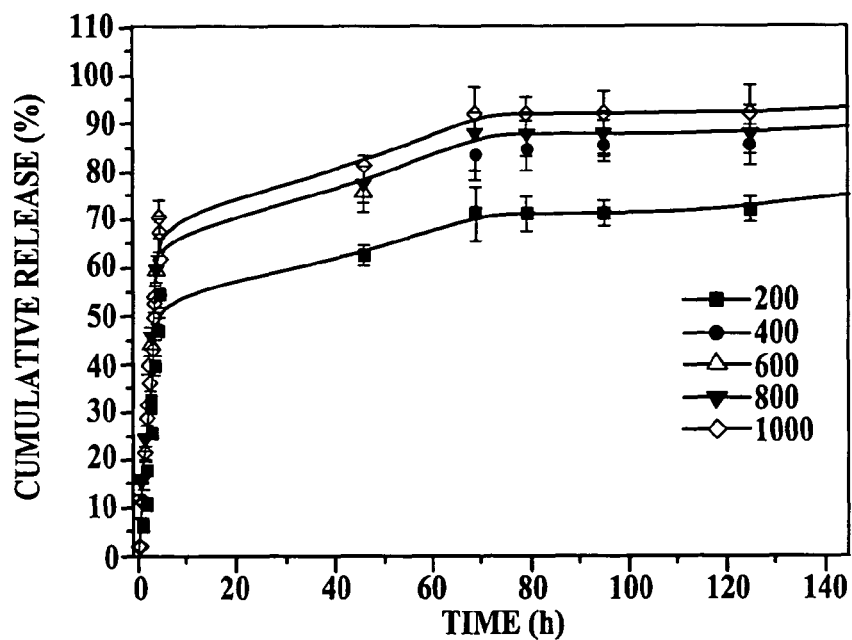
FIGS. 5A and B shows the percent cumulative release profiles of Bovine Serum Albumin (BSA) from thermoreversible gel G55 (FIG. 5A) and G45 (FIG. 5B) loaded with different concentrations of BSA, as described in Example 2. Each data point represents the mean value±SEM (n=3).
Figure 5B:
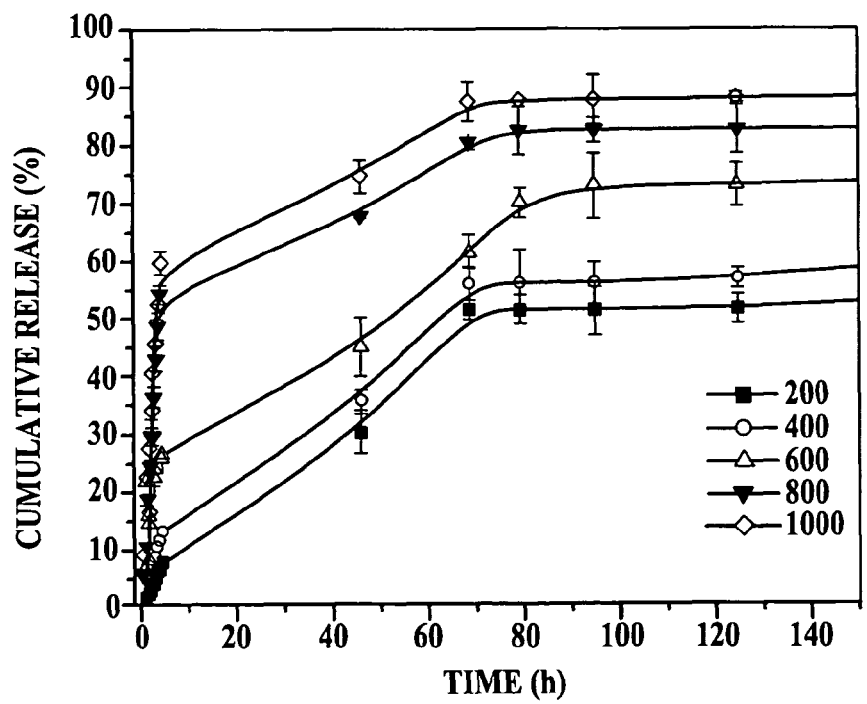

BSA Release from Gels:

Gels made from G55 and G45 PEG-g-chitosan were used for the BSA release study. FIGS. 5A and B show the percent cumulative release profiles of the gel matrices loaded with BSA of different concentrations ranging from 200 to 1000 μg/ml. Two distinctive release characteristics were seen for gels made from G55 and G45. The G55 gel showed a release of 52-67% of BSA in the first 5 hours, whereas the G45 gel showed a release of 10-58% of BSA in the same time period. Both G45 and G55 showed slow BSA release in the period of 5 to 70 hours and no apparent release thereafter. Clearly, after 70 hours, the remaining BSA was trapped in the gel matrix and could not be completely released until the gel matrix was dissolved in media.

Figure 6:
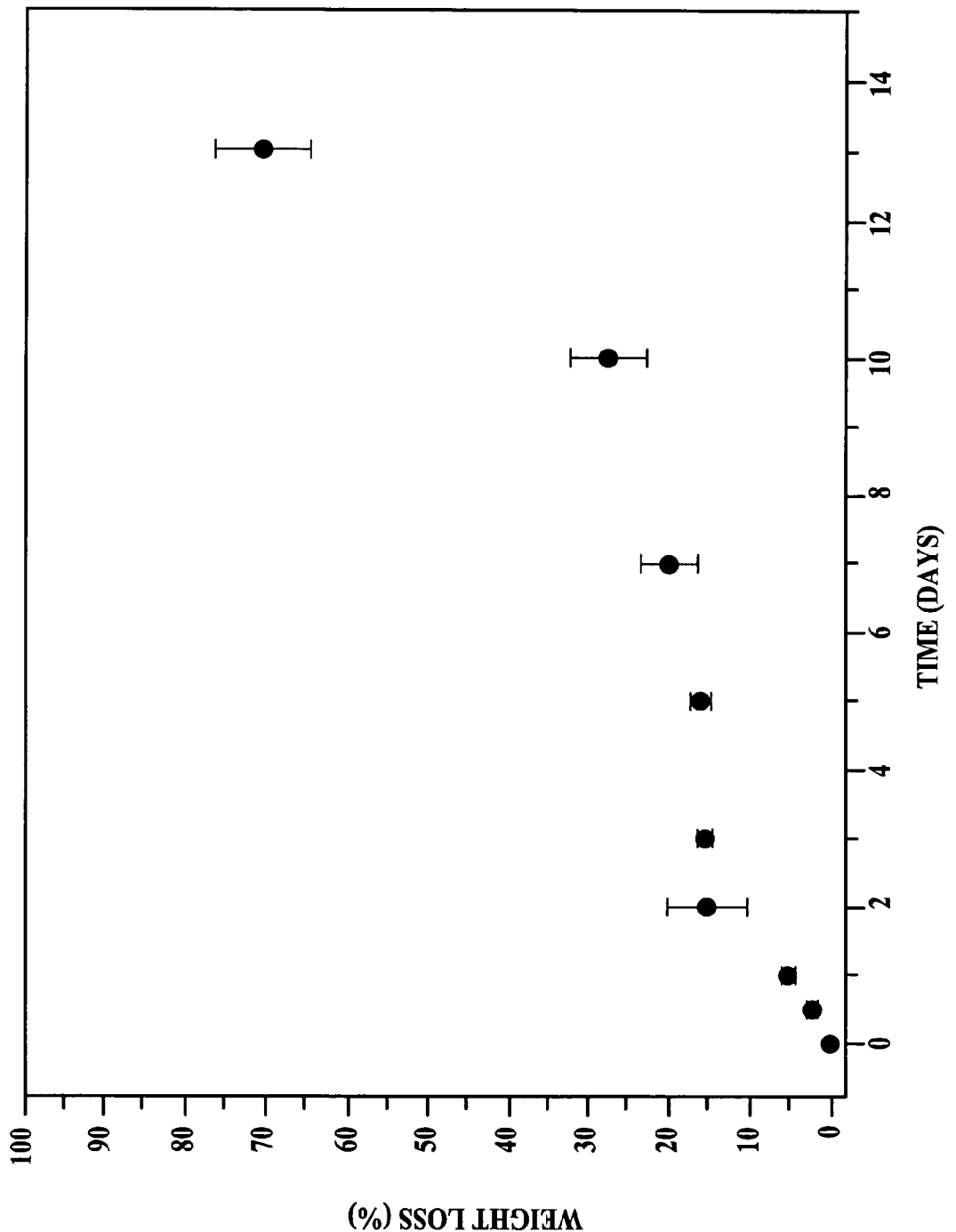
FIG. 6 shows the weight loss (due to dissolution) of gel G55 as a function of immersion time in PBS (pH=7.4) at 37° C.

Typically, G55 gels dissolved in PBS (pH 7.4) in around 2 weeks and G45 gels dissolved in around 3 weeks. FIG. 6 is one of the representative curves showing the dissolution, within two weeks, of G55 gel immersed in PBS. PEG-g- chitosan gels were placed into glass vials and maintained at a desired temperature under the same conditions used in the BSA release studies. At predetermined time intervals, the gels were separated from the release medium, washed with DI water and gently blotted. Then, they were freeze-dried for 48 hours and weighed again. Approximately 18% of the dry weight was lost in the first 48 hours, and only about 10% during the following week (FIG. 6). The most significant weight loss occurred around 2 weeks.

In general, gels loaded with BSA at different concentrations exhibited a similar trend in cumulative BSA release, except for the initial "burst" release which exhibited a cumulative release proportional to BSA loading. Gels of this type are suitable for short-term drug release, such as release over a period of hours or days.

Genipin-Treated PEG-g-Chitosan Gel:

Genipin solution having a concentration of 0.5 mM was added to the PEG-g-chitosan solution and mixed at 10° C. under constant stirring. The mixture was then maintained at a temperature of 37° C. The crosslinking of the gel completed within several hours, and was characterized by a change in color from transparent to light yellow and to deep blue. The color change is due to the formation of a crosslinked network by the reaction of chitosan fragments in PEG-g-chitosan with genipin (F. L. Mi et al., *J. Polym. Sci. Pol. Chem.* 38:2804-14, 2000). As the reaction proceeded the viscosity of the solution increased. FTIR and viscosity measurements were made to estimate the networking reaction time after the genipin treatment. The spectra of the genipin treated samples as compared to the spectra of non-treated samples showed a significant decrease in adsorption at 1570 cm$^{-1}$, which may be attributable to the absorption of NH$_2$ group as a result of the reaction between the chitosan portion of PEG-chitosan and genipin. This decrease in adsorption is particularly significant after 3 hours reaction. Besides all the characteristic peaks corresponding to PEG and chitosan segments, the new peak at ~1380 cm$^{-1}$ is attributable to the ring-stretching of heterocyclic amine in the gel network.

Figure 7:
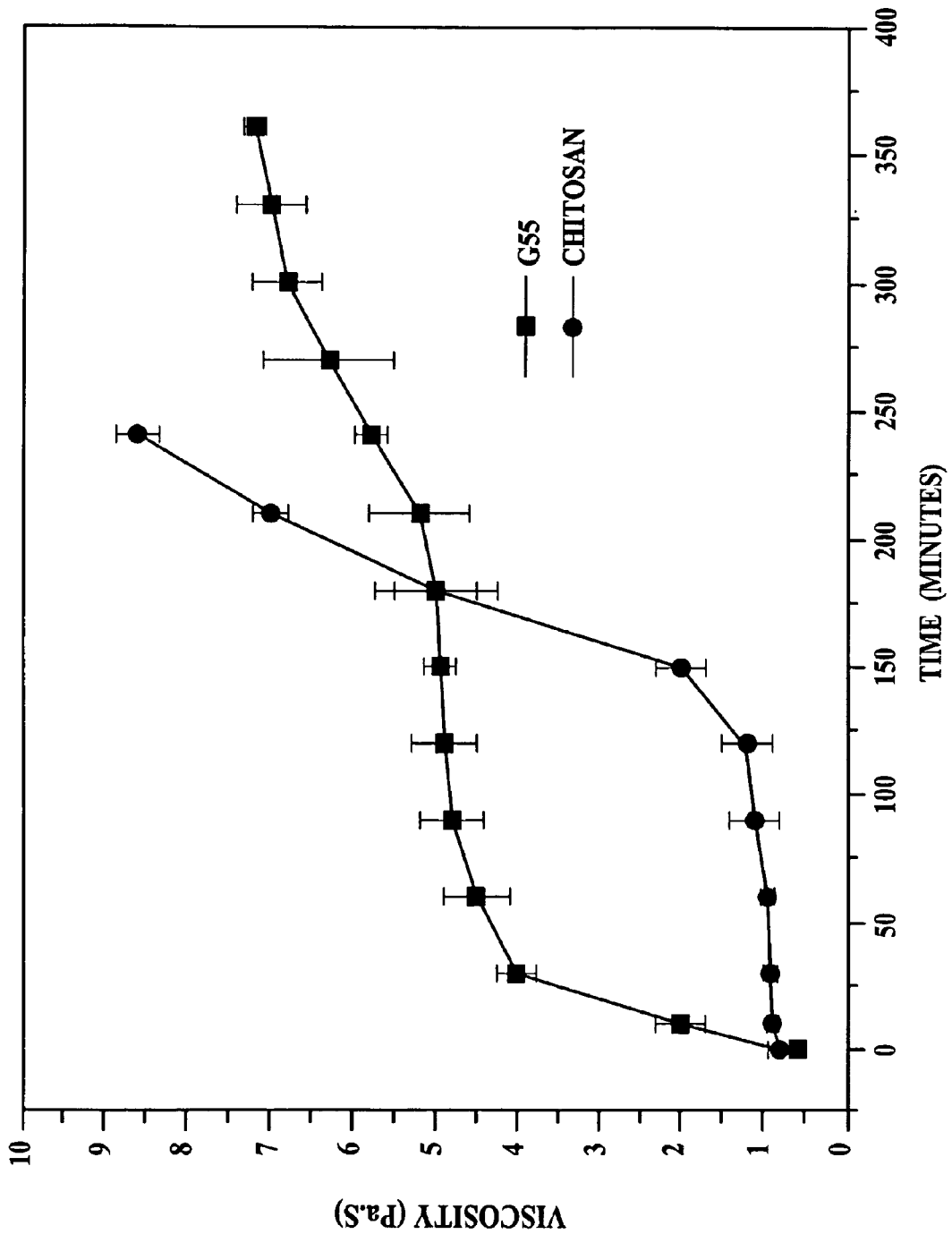
FIG. 7 shows graphs of viscosity versus time for PEG-g-chitosan (G55) and pure chitosan during gelation in the presence of genipin. Polymer concentrations of PEG-g-chitosan and chitosan solutions were both 3 wt %, and the final concentration of genipin was 0.5 mM. Solutions were prepared at 10° C. and the viscosities were measured at 37° C.

The crosslinking reaction and the reaction time frame were further studied by measuring the viscosity of the gel solution during gelation. The result is shown in FIG. 7, along with the viscosity profile for a chitosan solution with genipin under the same conditions for comparison. The viscosity of the genipin-crosslinked PEG-g-chitosan solution increased noticeably at two distinct stages, as opposed to the single stage exhibited by the chitosan solution. The first rapid increase in viscosity for the PEG-g-chitosan solution is due to its thermoreversible nature, whereas the second increase is due to the networking reaction caused by genipin. The viscosity of the chitosan solution started to increase abruptly after 2 hours reaction, whereas the second increase in viscosity for PEG-g-chitosan solution started about 4 hours after reaction. This result shows that the gelation rate due to the networking reaction is faster with chitosan solution than with PEG-g-chitosan. The slower reaction rate in PEG-g-chitosan is probably due to the presence of fewer reactive amine groups and the steric hindrance created by the PEG segments.

Figure 8:
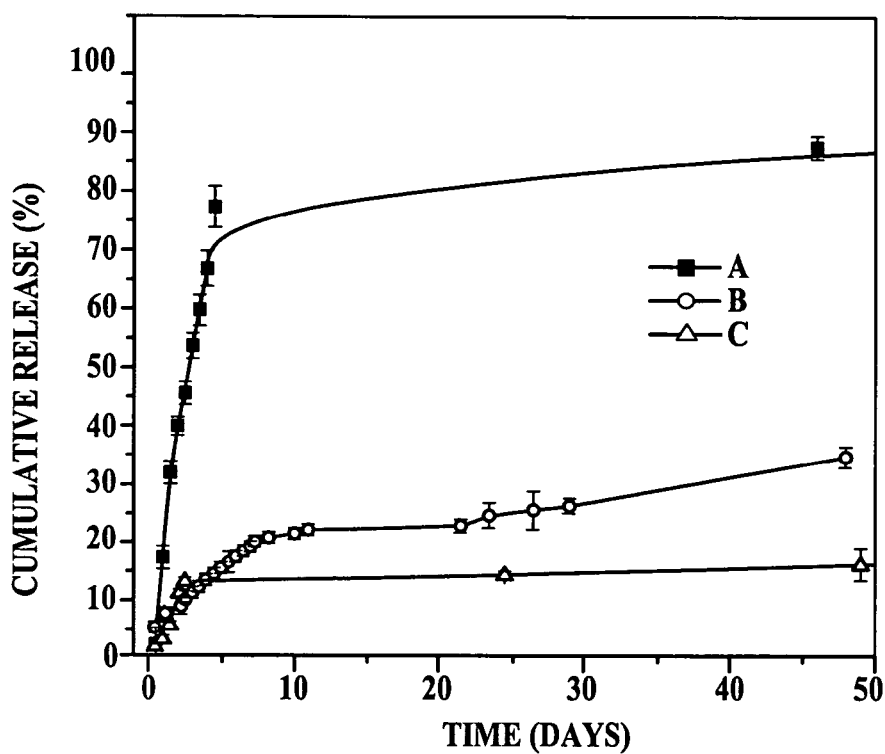
FIG. 8 shows graphs of cumulative percentage release of BSA from PEG-g-chitosan gels in vitro: (A) G55, (B) G55 treated with genipin for 10 minutes, and (C) G55 treated with genipin for 24 hours, as described in Example 2. All the gels contained the same amount of BSA (1000 µg/ml), and BSA was released into PBS (pH=7.4). The concentration of genipin was 0.5 mM. Triplicates for each gel were analyzed and each data point represents the mean value±SEM.

BSA Released from PEG-g-Chitosan Gels Crosslinked with Genipin:

To achieve prolonged protein release, PEG-g-chitosan gels were crosslinked with genipin in situ. PEG-g-chitosan solutions pre-loaded with BSA were mixed with genipin solution at 4° C., and protein released from the mixtures was monitored upon gelation at 37° C. FIG. 8 shows BSA release profiles of three types of samples over a 50 hour period: (A) G55 gel loaded with 100 µg/ml BSA after 10 minute gelation, (B) G55 gel loaded with 100 µg/ml BSA and 0.5 mM genipin after 10 minute gelation, and (C) G55 gel loaded with 100 µg/ml BSA and 0.5 mM genipin after 24 hour gelation. In each case, the original gel volume and BSA concentration were the same. The addition of genipin did not seem to affect the injectability of the gel solution after the mixture was cooled to 4° C. for 24 hours. However, the solutions with incorporated genipin lost thermoreversibility at 37° C., and the color of the gels changed from transparency to yellow within 2 hours and later changed to blue.

Figure 9:
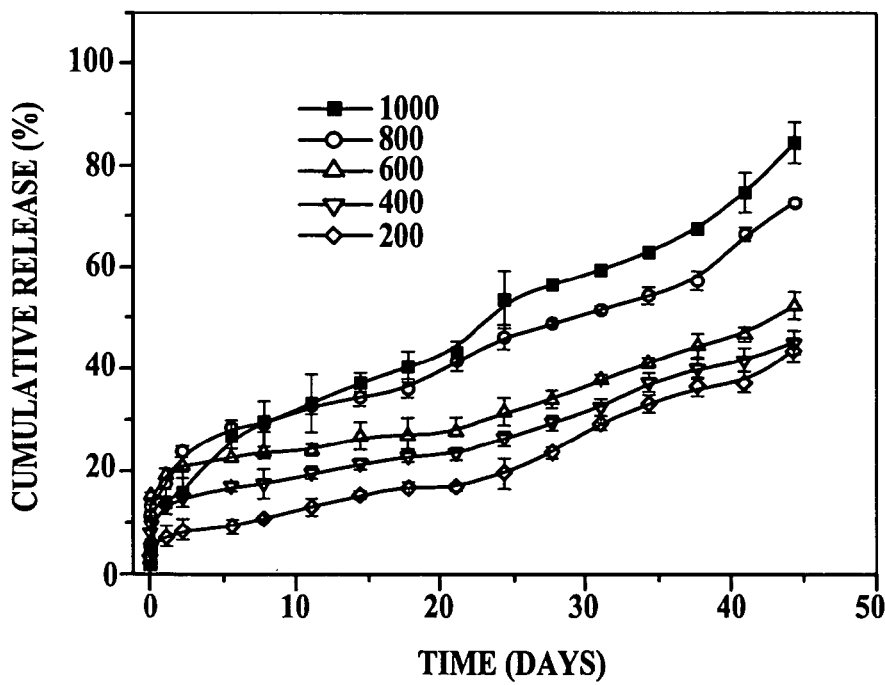
FIG. 9 shows a graph of the cumulative percentage release of BSA, over a period of 40 days, from G55 gels having BSA concentrations ranging from 200 to 1000 µg/ml. All the gels were pre-treated with genipin for 24 hours. The release study was performed in PBS (pH 7.4) in vitro. Concentration of genipin was 0.5 mM. Triplicates for each gel were analyzed and each data point represents the mean value±SEM.

As expected, crosslinking gels with genipin prolonged the BSA release profile of the gels. The gel without genipin released more than 70% of BSA in the first 5 hours, while the gel crosslinked with genipin for 24 h released only about 12% of BSA in the first day and another 30% in one week (release profile for extended period is shown in FIG. 9). For the gel treated with genipin for only 10 minutes, about 15% of BSA was released within the first day and another approximately 25% of BSA in two days.

FIG. 9 shows the cumulative release profiles of BSA, over a period of 40 days, of G55 gels with different BSA loading concentrations that have been crosslinked with genipin for 24 hours. The BSA release rate rose with an increase in the amount of BSA loaded in the gel. The release profiles exhibited a fast release rate in the first 5 hours, followed by a virtually linear release over a 40-day period.

Morphology of Freeze-Dried Gels as Determined by SEM:

The structures of G45 and G55 gels were examined by scanning electron microscopy (SEM) after releasing proteins in PBS at 37° C. for different time periods. The samples collected were frozen in liquid nitrogen and dried by freeze-drying. After 24 hours of BSA release, the gel exhibited a pore size of 15 to 30 µm. For both gels (G45 and G55), no apparent changes in surface morphology were observed in the first 24 hours of protein release in PBS. Both morphologies exhibited larger pore sizes and rougher surfaces after the gels were immersed in PBS for 2 weeks.

Drastic changes in porosity were observed after the gels were treated with genipin. These gels showed relatively low porosity after immersion in PBS for both one day and two weeks. Observation of genipin-treated samples immersed for different periods of time up to one month did not reveal a substantial change in porosity.

BSA Structural Integrity:

Exposure of BSA to an ionic solution and crosslinking agents could affect protein structure and stability (J. F. Foste, in V. M. Rosenoer, M. A. Oratz and M. A. Rothschild, eds., *Albumin Structure, Function and Uses*, Pergamon Press, Oxford, 1977, p. 53.). Possible detrimental effects of this process include protein denaturation, aggregation, hydrolysis, and reaction with the crosslinking agents, all of which could decrease the activity of proteins encapsulated in gels. Therefore, the effect of the gel environment on the integrity of encapsulated BSA was investigated using HPLC and SDS-PAGE. Both experiments were carried out on the BSA released from gels of G45 for 3 days (with and without genipin treatment) and compared with the original BSA in solution (i.e., a BSA standard). The following samples were analyzed using HPLC: standard BSA, BSA released from a non-crosslinked gel, and BSA released from a genipin-crosslinked gel.

It was noted that for all the samples there was a major and a minor component peak, labeled as α and β regions, respectively. Comparing the elution pattern with those obtained for standard albumin as reported by the column manufacturer (Life Sciences Solutions, Product Catalog Waters Corporation, 2004) as well as with those from the literature (A. K. Hunter, G. Carta, *J. Chromatogr., A* 937, 13-19, 2001), the major component peak was identified as BSA monomer and the minor component peak as the BSA oligomers (or mixture of BSA dimer, trimer, tetramer, etc.). The results showed that the major portion of BSA released from the gels was monomer, although the ratio of BSA monomer to oligomer in standard BSA is higher than in the released solutions. This observation suggests that the majority of BSA released from gels retain their integrity.

SDS-PAGE analysis revealed that BSA released from the gels, without and with genipin treatment, have distinct dark bands present at 66 kDa, indicating that the integrity of the released protein is largely retained. However, the presence of faint bands corresponding to higher molecular weights suggested that a small portion of the protein was multimers, which is consistent with the results obtained by HPLC. No bands corresponding to lower molecular weights were observed, suggesting that the released BSA did not undergo hydrolysis.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A composition comprising a crosslinked interpolymer of chitosan and polyethylene glycol, wherein chitosan is covalently coupled to polyethylene glycol in the interpolymer through a —NH—$CH_2$— linkage, the —NH— of the —NH—$CH_2$— linkage derived from chitosan and the —$CH_2$— of the —NH—$CH_2$— linkage derived from polyethylene glycol, wherein the chitosan has an average molecular weight from 190,000 to about 2,000,000 Daltons, wherein the polyethene glycol is present in the interpolymer in an amount of from 45% by weight to 55% by eight based on the total weight of the interpolymer, and wherein the composition is a liquid below 25° C. and a gel above 35° C.

2. The composition of claim 1, wherein the interpolymer is crosslinked with a crosslinking agent selected from the group consisting of genipin and glutaraldehyde.

3. The composition of claim 1, wherein the crosslinking agent is genipin.

4. The composition of claim 1, further comprising a growth factor.

5. The composition of claim 1, further comprising a cytokine.

6. The composition of claim 1, further comprising a biologically active molecule selected from the group consisting of a protein, a peptide, a lipid, an antibody, and a nucleic acid molecule.

7. A method for delivering a drug to a living body, the method comprising the step of delivering a composition comprising a drug to a portion of a living body, wherein:
the composition comprises a crosslinked interpolymer of chitosan and polyethylene glycol, wherein chitosan is covalently coupled to polyethylene glycol in the interpolymer through a —NH—$CH_2$— linkage, the —NH— of the —NH—$CH_2$— linkage derived from chitosan and the —$CH_2$— of the —NH—$CH_2$— linkage derived from polyethylene glycol, wherein the chitosan has an average molecular weight from 190,000 to about 2,000,000 Daltons, wherein the polyethylene glycol is present in the interpolymer in an amount of from 45% by weight to 55% by weight based on the total weight of the interpolymer, and wherein the composition is a liquid below 25° C. and a gel above 35° C.

8. The method of claim 7, wherein the interpolymer is crosslinked with a crosslinking agent is selected from the group consisting of genipin and glutaraldehyde.

9. The method of claim 7, wherein the drug is selected from the group consisting of a protein, a peptide, a lipid, an antibody, and a nucleic acid molecule.

10. The method of claim 7, wherein the composition comprises a growth factor.

11. The method of claim 7, wherein the composition comprises a cytokine.

12. A method for delivering a drug to a living body, the method comprising the step of delivering a composition comprising a drug to a portion of a living body, wherein:
the composition comprises a crosslinked interpolymer of chitosan and polyethylene glycol and a growth factor that promotes the growth of bone, wherein chitosan is covalently coupled to polyethylene glycol in the interpolymer through a —NH—$CH_2$— linkage, the —NH— of the —NH—$CH_2$— linkage derived from chitosan and the —$CH_2$— of the —NH—$CH_2$— linkage derived from polyethylene glycol, wherein the chitosan has an average molecular weight from 190,000 to about 2,000,000 Daltons, wherein the polyethylene glycol is present in the interpolymer in an amount of from 45% by weight to 55% by weight based on the total weight of the interpolymer, and wherein the composition is a liquid below 25° C. and a gel above 35° C.

13. A composition made by a process comprising the step of covalently linking polyethylene glycol to chitosan to form an interpolymer of chitosan and polyethylene glycol and crosslinking the interpolymer with a crosslinking agent to provide a crosslinked interpolymer of chitosan and polyethylene glycol, wherein chitosan is covalently coupled to polyethylene glycol in the interpolymer through a —NH—$CH_2$— linkage, the —NH— of the —NH—$CH_2$— linkage derived from chitosan and the —$CH_2$— of the —NH—$CH_2$— linkage derived from polyethylene glycol, wherein the chitosan has an average molecular weight from 190,000 to about 2,000,000 Daltons, wherein the polyethylene glycol is present in the interpolymer in an amount from 45% by weight to 55% by weight based on the total weight of the interpolymer, and wherein the composition is a liquid below 25° C. and a gel above 35° C.

14. A composition, comprising an interpolymer of chitosan and polyethylene glycol, wherein chitosan is covalently coupled to polyethylene glycol in the interpolymer through a —NH—$CH_2$— linkage, the —NH— of the —NH—$CH_2$— linkage derived from chitosan and the —$CH_2$— of the —NH—$CH_2$— linkage derived from polyethylene glycol, wherein the polyethylene glycol is present in the interpolymer in an amount of from 45% by weight to 55% by weight based on the total weight of the interpolymer, and wherein the composition is a liquid below 25° C. and a gel above 35° C.

15. The composition of claim 14 further comprising a growth factor.

16. The composition of claim 14 further comprising a cytokine.

17. The composition of claim 14 further comprising a biologically active molecule selected from the group consisting of a protein, a peptide, a lipid, an antibody, and a nucleic acid molecule.

18. The composition of claim 14, wherein the interpolymer is a crosslinked interpolymer.

* * * * *

UNITED STATES PATENT AND TRADEMARK OFFICE
CERTIFICATE OF CORRECTION

PATENT NO. : 8,663,686 B2  
APPLICATION NO. : 11/124916  
DATED : March 4, 2014  
INVENTOR(S) : M. Zhang et al.

Page 1 of 1

It is certified that error appears in the above-identified patent and that said Letters Patent is hereby corrected as shown below:

In the Claims:

| COLUMN | LINE | ERROR |
|---|---|---|
| 17 (Claim 1, line 10) | 34 | "eight" should read --weight-- |

Signed and Sealed this  
Seventh Day of October, 2014

Michelle K. Lee  
*Deputy Director of the United States Patent and Trademark Office*